United States Patent [19]

Ikawa et al.

[11] Patent Number: 5,382,720
[45] Date of Patent: Jan. 17, 1995

[54] PREPARATION OF DIMER OF FLUORINE-CONTAINING ETHANE

[75] Inventors: Tsuneo Ikawa, Kamakura; Yutaka Morikawa; Wataru Ueda, both of Machida, all of Japan

[73] Assignee: Daikin Industries, Ltd., Osaka, Japan

[21] Appl. No.: 144,546

[22] Filed: Nov. 1, 1993

Related U.S. Application Data

[63] Continuation of Ser. No. 835,591, Feb. 14, 1992, abandoned.

[30] Foreign Application Priority Data

Feb. 16, 1991 [JP] Japan ................... 3-022414

[51] Int. Cl.⁶ .................. C07C 17/02; C07C 17/28
[52] U.S. Cl. ........................... 570/153; 570/171
[58] Field of Search ................ 570/153, 159, 171

[56] References Cited

U.S. PATENT DOCUMENTS

| | | | |
|---|---|---|---|
| 2,551,573 | 5/1951 | Downing | 570/159 |
| 2,644,835 | 7/1953 | Ladd et al. | |
| 3,799,996 | 3/1974 | Bloch | 570/159 |

FOREIGN PATENT DOCUMENTS

| | | |
|---|---|---|
| 0190594 | 8/1986 | European Pat. Off. |
| 0376856 | 7/1990 | European Pat. Off. |
| 2204313 | 11/1988 | United Kingdom |

OTHER PUBLICATIONS

Cotton Advanced Inorg Chem 2nd ed (1966) p. 722.
W. Theilheimer "Synthetische Methoden der Organischen Chemie Band 4", 1966, S. Karger, Basel, CH, p. 286, reaction 796.

*Primary Examiner*—Alan Siegel
*Attorney, Agent, or Firm*—Birch, Stewart, Kolasch & Birch

[57] ABSTRACT

A dimer of fluorine-containing ethane can be obtained in a good selectivity by contacting fluorine-containing ethane of the formula:

$$CF_3-CClX^1X^2 \qquad (I)$$

wherein each of $X^1$ and $X^2$ is a fluorine or chlorine atom to a nickel catalyst.

9 Claims, No Drawings

PREPARATION OF DIMER OF FLUORINE-CONTAINING ETHANE

This application is a continuation of application Ser. No. 07/835,591 filed on Sept. 14, 1992, now abandoned.

BACKGROUND OF THE INVENTION

1. Field of the Invention

The present invention relates to a method for preparing a dimer of fluorine-containing ethane.

2. Description of related art

A dimer of fluorine-containing ethane, for example $CF_3CCl=CClCF_3$ is useful as a monomer of a polymer. However, a method for preparing the dimer of fluorine-containing ethane in a good selectivity is not known.

SUMMARY OF THE INVENTION

An object of the present invention is to prepare a dimer of fluorine-containing ethane from fluorine-containing ethane in a good selectivity.

This and other objects of the present invention are achieved by a method for preparing a dimer of fluorine-containing ethane of the formula:

$$CF_3-CClX^1X^2 \tag{I}$$

wherein each of $X^1$ and $X^2$ is a fluorine or chlorine atom to a catalyst comprising nickel.

DETAILED DESCRIPTION OF THE INVENTION

Specific examples of fluorine-containing ethane (I) are 1,1,1-trichloro-2,2,2-trifluoroethane ($CF_3CCl_3$, R-113a), 1,1-dichloro-1,2,2,2-tetrafluoroethane ($CF_3CFCl_2$, R-114a) and 1-chloro-1,1,2,2,2-pentafluoroethane ($CF_3CF_2Cl$ R-115).

The catalyst comprises nickel. The nickel catalyst is nickel metal as such or nickel metal supported on a carrier. Specific examples of the carrier are $SiO_2$, $Al_2O_3$, activated carbon, MgO, $TiO_2$ and $SiO_2-Al_2O_3$. When nickel is supported on the carrier, an amount of nickel is 0.1 to 20 parts by weight based on the total weight of nickel and the carrier. Although the particle size of the catalyst is not critical, it is preferably from 16 to 60 mesh.

The supported catalyst may be prepared by any one of several known methods. An $Ni/SiO_2$ catalyst which contains Ni supported on $SiO_2$ can be prepared by, for example, adding silica Aerosil ® to an aqueous solution of nickel nitrate and then evaporating the mixture to dryness. An $Ni/Al_2O_3$ catalyst which contains Ni supported on $Al_2O_3$ can be prepared by, for example, adding alumina Aerosil ® to an aqueous solution of nickel nitrate and then evaporating the mixture to dryness. An Ni/C catalyst which contains Ni supported on activated carbon can be prepared by, for example, adding activated carbon to nickel nitrate, fully mixing them and then drying the mixture.

Specific examples of the dimer of fluorine-containing ethane prepared according to the present invention are fluorine-containing butane of the formula:

$$CF_3CY^1Y^2-CY^3Y^4CF_3 \tag{II}$$

wherein each of $Y^1$, $Y^2$, $Y^3$ and $Y^4$ is a hydrogen, chlorine or fluorine atom, fluorine-containing 2-butene of the formula:

$$CF_3CY^1=CY^3CF_3 \tag{III}$$

wherein each of $Y^1$ and $Y^3$ is a hydrogen, chlorine or fluorine atom, and perfluorinated 2-butyne of the formula:

$$CF_3C≡CCF_3 \tag{IV}$$

A hydrogen gas is preferably used in the method of the present invention. The hydrogen gas can regenerate the catalyst. The amount of the hydrogen gas is usually from 0.5 to 10 mol, preferably from 2 to 6 mol per one mol of fluorine-containing ethane.

Preferably, the reaction in the present invention is conducted in a continous process. The feed rate of a feed gas (SV) is preferably 100 to 10,000 ($h^{-1}$). SV is herein defined as $$\frac{[\text{feed gas volume per unit time (at reaction temperature)}]}{[\text{apparent filled volume of catalyst}]}.$$

The reaction pressure is not limited, and any practical reaction pressure can be used. The reaction temperature is usually from 200 to 550° C., preferably from 290 to 450° C. When the reaction temperature is lower than 200° C., the conversion is low. When it is higher than 550° C., the selectivity is low and the catalyst is deteriorated. The reaction gas may be used as such, or the reaction gas may be diluted by a gas which has no effect on the reaction, such as $N_2$, Ar and He.

PREFERRED EMBODIMENTS OF THE INVENTION

The present invention will be illustrated by the following Examples which do not limit the present invention.

Examples 1

Silica Aerosil ® was added to an aqueous solution of nickel nitrate and the mixture was evaporated to dryness. Then, the mixture was dried at 120° C. for one day to prepare a catalyst ($Ni/SiO_2$) having a nickel amount of 1% by weight (particle size: 32 to 60 mesh). Before the reaction, the catalyst was not calcined at a high temperature.

In a normal pressure fixed bed reaction apparatus (internal diameter of a reaction tube: 12.5 mm), a pretreatment for reducing the catalyst was conducted at 450° C. for two hours in an $H_2$ stream before the reaction. A feed gas consisting of R-113a (10 $cm^3$/min.), Ar (56 $cm^3$/min.) and $H_2$ (29 $cm^3$/min.) was fed at a flow rate of 95 $cm^3$/min. The reaction temperature was 450° C. and an amount of the catalyst was 1 g. Hydrogen halide generated by the reaction was absorbed by calcium oxide and a resultant gas was analyzed by a gas chromatography. A GC-mass spectrometer was used so as to identify a product in a small amount. The conversion of R-113a and selectivities of resultant products after reaction for 2 hours are shown in Table 1. Also after reaction for 1 hour or 6 hours, the convension was 100% and selectivities of $CF_3CCL=CClCF_3$, $CF_3CH=CClCF_3$ and $CF_3CH=CHCF_3$ were high.

Comparative Example 1

The procedure in Example 1 was repeated except that a $Cr/SiO_2$ catalyst was used instead of the $Ni/SiO_2$ catalyst. An amount of Cr in the $Cr/SiO_2$ catalyst was 1% by weight and the particle size of the catalyst was 32 to 60 mesh. The Cr/SiO$_2$ catalyst was prepared by adding silica Aerosil ® to an aqueous solution of chromium nitrate, evaporating the mixture to dryness and then drying the mixture at 120° C. for one day. Before the reaction, the catalyst was not calcined at a high temperature. The conversion and selectivities of the products after reaction for 2 hours are shown in Table 1.

TABLE 1

|  | Example 1 | Com. Example 1 |
|---|---|---|
| Conversion (%) | 100 | 27.5 |
| Selectivity (%) |  |  |
| R-1112 | (trace) | 30.5 |
| R-1111 | 0 | 6.9 |
| R-114a | 0 | 37.9 |
| R-123 | 0 | 4.3 |
| CF$_3$CCl=CClCF$_3$ | 85.8 | 0 |
| CF$_3$CH=CClCF$_3$ | 4.8 | 0 |
| CF$_3$CH=CHCF$_3$ | 6.0 | 0 |

Example 2

The procedure in Example 1 was repeated except that R-114a was used instead of R-113a in the feed gas. The conversion and selectivities of products after the reaction for two hours are shown in Table 2.

Comparative Example 2

The procedure in Comparative Example 1 was repeated except that R-114a was used instead of R-113a in the feed gas. The conversion and selectivities of products after reaction for two hours are shown in Table 2.

TABLE 2

|  | Example 2 | Com. Example 2 |
|---|---|---|
| Conversion (%) | 4.5 | 72.6 |
| Selectivity (%) |  |  |
| R-1113 | 0 | 0.6 |
| R-1112 | 0 | 8.2 |
| R-1111 | 0 | 10.0 |
| R-115 | 0 | 48.0 |
| R-112a | 0 | 1.5 |
| R-124 | 56.9 | 0.3 |
| R-1110 | 0 | 3.5 |
| CF$_3$CClF—CClFCF$_3$ | 11.5 | 0 |

According to the present invention, the dimer of fluorine-containing ethane can be obtained in a good selectivity. Fluorine-containing 2-butene and perfluorinated 2-butyne which are the dimers of fluorine-containing ethane can be used as a copolymerizable monomer used for preparing a polymer having high temperature resistance and/or electrical conductivity.

What is claimed is:

1. A method for preparing a dimer of a fluorine-containing ethane, which comprises contacting in the gas phase a fluorine-containing ethane of the formula:

$$CF_3-CCl\ X^1\ X^2 \qquad (I)$$

wherein each of $X^1$ and $X^2$ is a fluorine or chlorine atom, with a catalytic amount of a catalyst selected from the group consisting of metallic nickel and metallic nickel supported on a carrier in the presence of hydrogen gas, and obtaining therefrom said fluorine-containing ethane dimer.

2. The method according to claim 1, wherein the carrier is one selected from the group consisting of SiO$_2$, Al$_2$O$_3$, activated carbon, MgO, TiO$_2$ and SiO$_2$—Al$_2$O$_3$.

3. The method according to claim 1, wherein fluorine-containing ethane is one selected from the group consisting of 1,1,1-trichloro-2,2,2-trifluoroethane, 1,1,-dichloro-1,2,2, 2-tetrafluoroethane and 1-chloro-1,1,2,2,2-pentafluoroethane.

4. The method according to claim 1, wherein the dimer of fluoroin-containing ethane is one selected from the group consisting of fluorine-containing butane of the formula:

$$CF_3CY^1Y^2-CY^3Y^4CF_3 \qquad (II)$$

wherein each of $Y^1$, $Y^2$, $Y^3$ and $Y^4$ is a hydrogen, chlorine or fluorine atom, fluorine-containing 2-butene of the formula:

$$CF_3CY^1=CY^3CF_3 \qquad (III)$$

wherein each of $Y^1$ and $Y^3$ is a hydrogen, chlorine or fluorine atom, and perfluorinated 2-butyne of the formula:

$$CF_3C\equiv CCF_3 \qquad (IV)$$

5. The method according to claim 1, wherein said catalyst has a particle size of 16 to 60 mesh.

6. The method according to claim 1, wherein said contacting is carried out as a continuous process.

7. The method according to claim 1, wherein said contacting is carried out at a feed rate of 100 to 10,000 h$^{-1}$ and a temperature of 200° to 550° C.

8. The method according to claim 1, wherein said contacting is carried out in the presence of a diluent gas.

9. The method according to claim 1, wherein said catalyst contains said nickel in an amount of 0.1 to 20 parts by weight based on the total weight of said nickel and said carrier.

* * * * *